United States Patent
Thangaraju et al.

(10) Patent No.: US 9,867,993 B2
(45) Date of Patent: Jan. 16, 2018

(54) SYSTEM AND METHOD FOR GENERATING ELECTRIC CHARGES FROM HEART TO POWER IMPLANTABLE MEDICAL DEVICES

(71) Applicants: Shyam Thangaraju, Chennai (IN); Siva Sakthivel, Chennai (IN); Vishal Chaudhary, Noida (IN)

(72) Inventors: Shyam Thangaraju, Chennai (IN); Siva Sakthivel, Chennai (IN); Vishal Chaudhary, Noida (IN)

(73) Assignee: HCL TECHNOLOGIES LIMITED, Chennai (IN)

( * ) Notice: Subject to any disclaimer, the term of this patent is extended or adjusted under 35 U.S.C. 154(b) by 662 days.

(21) Appl. No.: 14/525,235

(22) Filed: Oct. 28, 2014

(65) Prior Publication Data

US 2016/0114170 A1    Apr. 28, 2016

(51) Int. Cl.
*A61N 1/378* (2006.01)
*A61B 5/0245* (2006.01)
*A61B 5/04* (2006.01)
*A61B 5/00* (2006.01)
*A61B 5/0464* (2006.01)

(52) U.S. Cl.
CPC ........ *A61N 1/3785* (2013.01); *A61B 5/02455* (2013.01); *A61B 5/04001* (2013.01); *A61B 5/0031* (2013.01); *A61B 5/0464* (2013.01); *A61B 2560/0214* (2013.01)

(58) Field of Classification Search
CPC .................................................... A61N 1/3785
USPC ......................................................... 307/154
See application file for complete search history.

(56) References Cited

U.S. PATENT DOCUMENTS

| | | | |
|---|---|---|---|
| 2009/0171408 A1* | 7/2009 | Solem | A61B 5/0245 607/4 |
| 2012/0235634 A1* | 9/2012 | Hall | H03H 7/40 320/108 |

* cited by examiner

*Primary Examiner* — Joseph Chang
(74) *Attorney, Agent, or Firm* — Mannava & Kang, P.C.; Vinay Malik

(57) ABSTRACT

Disclosed herein is system and method for generating, storing and transmitting electrical charge from heart's electrical conduction system to power implantable medical devices. An intelligent monitoring module in the system monitors amount of nerve impulses that are generated at the Sinoatrial (SA) node of the heart and continuously compares number of the generated nerve impulses with a threshold nerve impulse value. If excess impulses are detected, the intelligent monitoring module routes the excess nerve impulses to a battery management module which generates charge by converting the excess nerve impulses to electric charge. This charge may be further used to power up the implantable medical device.

9 Claims, 5 Drawing Sheets

SYSTEM AND METHOD FOR GENERATING ELECTRIC CHARGES FROM HEART TO POWER IMPLANTABLE MEDICAL DEVICES

The present application is based on, and claims priority from, Indian Complete Application number 5266/CHE/2013 filed on 15 Nov. 2013, the disclosure of which is hereby incorporated by reference herein.

TECHNICAL FIELD

The embodiments herein relate to powering implantable medical devices and, more particularly, to generate, store and transmit electric charges from the heart's electrical conduction system to power the implantable medical devices.

BACKGROUND

The Implantable Medical Devices (IMD's) are instruments or apparatus or implants that are implanted inside body to diagnose or treat any disease or disorder present in the body. For proper functioning of these devices inside the body, sufficient power must be provided continuously by using suitable means such as batteries, power capacitors and so on. In some cases, these power sources can be placed outside the body and transmit energy pulses to the implanted devices through a receiver or a lead.

Over an extended period of time, these power sources may deplete which results in the implanted medical device not getting power. Due to this issue, the implanted medical device stops functioning permanently which in turn puts the patient's life at danger. Hence, the power sources must be powered or recharged periodically to ensure proper functioning of IMDs inside the body.

Normally, every IMD possesses a rechargeable battery which powers up the device. There are so many techniques through which this power sources i.e. rechargeable battery can be recharged. In some of the existing recharging mechanisms, piezoelectric effect based charging process is used. In some other existing systems, induction coils are placed with the implanted medical devices to supply power and theses coils are heated whenever the coils get discharged.

However, in the existing systems, input supply to charge the battery is provided continuously even if the battery is fully charged. This may have an adverse impact on the battery life, as it increases load on the battery. This in turn affects functioning of the IMD and this scenario may demand replacement of the battery or the IMD itself, which requires the patient to undergo a surgery. This is inconvenient in terms of factors such as cost incurred, health effects for patient and so on.

SUMMARY

In view of the foregoing, an embodiment herein provides a method for generating electric charge from electrical conduction system of heart to power up an implantable medical device (IMD). The method comprises of measuring periodicity value of heartbeat. Further, the measured periodicity value is compared with a normal range of periodicity value and if the measured periodicity value exceeds the normal range of periodicity value, then charge is generated from the electrical conduction system of heart.

Embodiments further disclose a system for generating electric charge for an implanted device from electrical conduction system of heart. The system is configured for measuring periodicity value of heart beat using an Implantable Medical Device (IMD) powering system environment. Further, the system compares the measured periodicity value with a normal range of periodicity value using the IMD powering system environment and if the measured periodicity value exceeds the normal range of periodicity value, then charge is generated from the electrical conduction system of heart using the IMD powering system environment.

These and other aspects of the embodiments herein will be better appreciated and understood when considered in conjunction with the following description and the accompanying drawings.

BRIEF DESCRIPTION OF THE FIGURES

The embodiments herein will be better understood from the following detailed description with reference to the drawings, in which.

DETAILED DESCRIPTION

Figure 1:
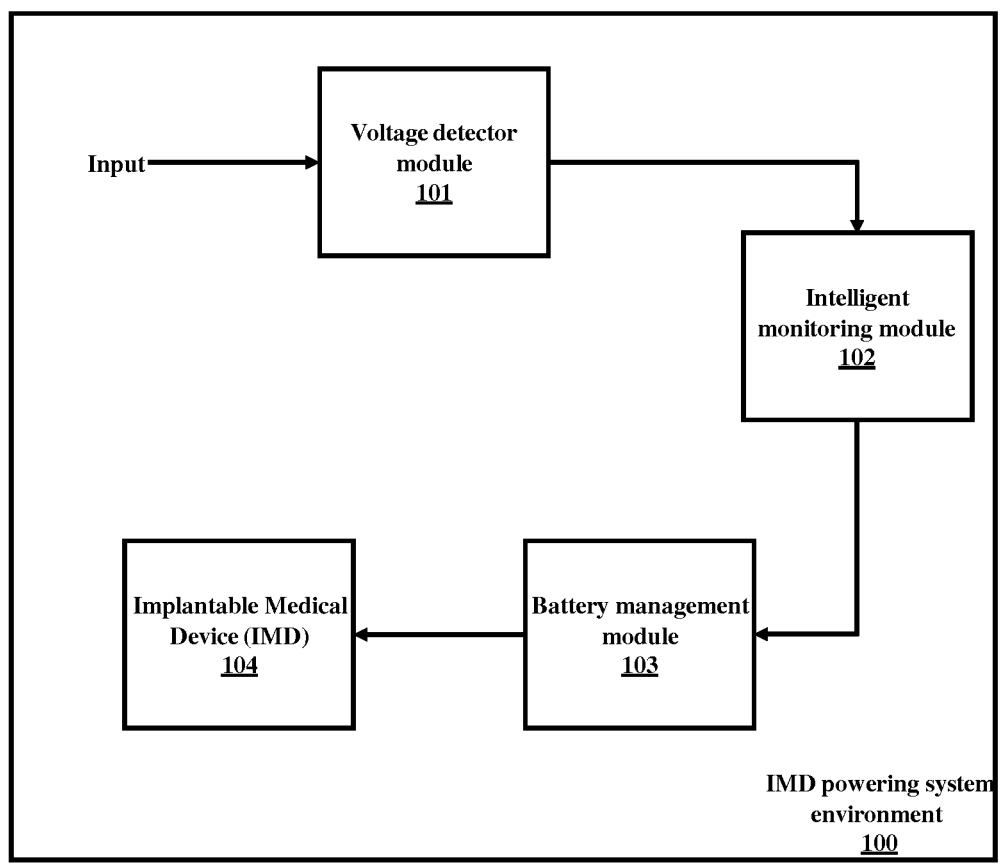
FIG. 1 illustrates a block diagram of an Implantable Medical Device (IMD) powering system environment, as disclosed in the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein disclose a system and method for powering IMDs by generating electric charges from heart's electrical conduction system. Referring now to the drawings, and more particularly to FIGS. 1 through 5, where similar reference characters denote corresponding features consistently throughout the figures, there are shown embodiments.

In human body, heart is a hollow muscular organ that pumps blood to various parts of the body. This is accomplished by contraction and relaxation of cardiac muscle tissues present in the myocardium layer of the heart. The electrical conduction system present in the heart controls the heart rate (i.e., contraction and relaxation of heart). This system creates electrical nerve impulses or action potentials or rhythmic firing and send them throughout the heart which makes the heart to contract and pump blood to various parts of the body.

The Sinoatrial (SA) node which is located in the back wall of the right atrium acts a natural pacemaker in the heart and initiates these nerve impulses without using any nerve stimulation from the brain. These nerve impulses get depolarized at a particular frequency (usually 60-100/min) which then travels to Atrioventricular (AV) node through inter-modal pathways and finally travels throughout the heart resulting in a 'heartbeat'. These self generated nerve impulses are derived by a minimum potential or minimum stimulus known as a 'pacemaker potential'. The electric current required to move the membrane potential from resting potential to the pacemaker potential is in order of few Pico Amperes.

While generating nerve impulses at SA node, the electric current required in the nerves follows all or none phenomenon i.e., each nerve takes a minimum stimulus (pacemaker potential) for generating nerve impulses and below that minimum stimulus no nerve impulses are generated. Any stimulus beyond that potential invokes a complete nerve impulse or action potential. Further, when a stronger stimulus came, the number of nerve impulses that are generated in the nerve increases but the actual size of the nerve impulses remains same. Thus, whenever a stronger stimulus came, excess number of nerve impulses are generated at the SA node. As minimum stimulus is enough to generate required nerve impulses, the excess nerve impulses that are generated at the SA node are useless and may not contribute for the heart's electrical conduction. Hence, these extra nerve impulses can be captured and used to generate electric charge which in turn may be used to power up the IMD's that are present inside the body.

FIG. 1 illustrates a block diagram of an Implantable Medical Device (IMD) powering system environment, as disclosed in the embodiments herein. The Implantable Medical Device (IMD) powering system environment 100 comprises of a voltage detector module 101, an intelligent monitoring module 102, a battery management module 103, and an IMD 104.

The voltage detector module 101 comprises of a voltage sensor which is clamped around the intermodal pathways present in the heart. The sensor present in the voltage detector module 101 detects the nerve impulses that are passed through the intermodal pathways of the heart. In an embodiment, the voltage detector module 101 can be a potentiometer or a patch clamp which can detect the generated nerve impulses.

The intelligent monitoring module 102 is a monitoring framework that manages and controls process of generating electric charges from the excess nerve impulses that are produced in the heart. To do this, the intelligent monitoring module 102 continuously monitors the electrical conduction system of heart. Further, the intelligent monitoring module 102 permits the battery management module 103 to capture the generated excess nerve impulses by routing the excess impulses to the battery management module 103. Moreover, the intelligent monitoring module 102 allows sufficient number of nerve impulses to pass from SA node to AV node and ensures the proper functioning of heart's electrical conduction system.

The battery management module 103 is an electric current sink with a charge management system that captures excess nerve impulses and generates electric charges for them. Further, the battery management module 103 stores the generated electric charge in a rechargeable battery associated with the battery management module 103. This charge may be then used to power up the IMD 104. Further, the battery management module 103 logs the charge status and regulates the inflow and outflow of the electric charge to and fro from the battery. Furthermore, the battery management module 103 can power the IMDs 104 inside the body by transmitting the stored electric charges from the battery to them. In an embodiment, the IMD 104 can be any instrument or apparatus or an implant that is implanted inside the body to diagnose or treat any disease or disorder present inside the body.

Figure 2:
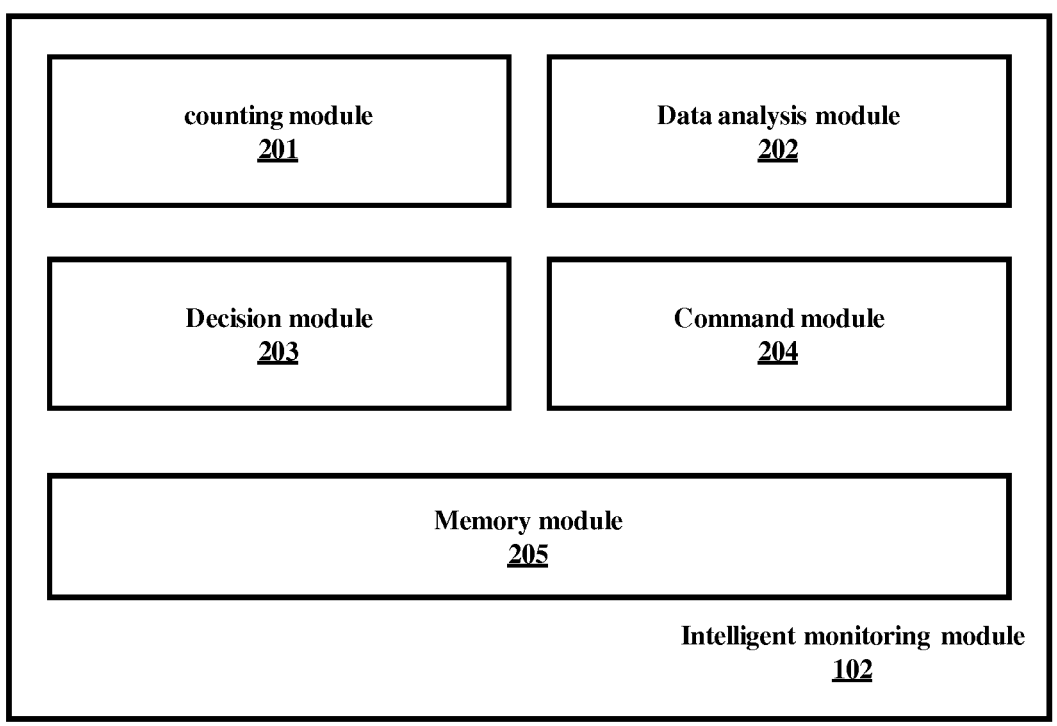
FIG. 2 is a block diagram that shows various components of intelligent monitoring module, as disclosed in the embodiments herein.

FIG. 2 is a block diagram that shows various components of intelligent monitoring module, as disclosed in the embodiments herein. The intelligent monitoring module 102 comprises of a counting module 201, a data analysis module 202, a decision module 203, a command module 204, and a memory module 205.

The counting module 201 recognizes the nerve impulses that are read by the voltage detector module 101. Further, the counting module 201 counts the recognized nerve impulses and sends a result to the data analysis module 202 which contains the count of total number of nerve impulses produced for single heart beat.

The data analysis module 202 receives the result from the counting module 201 and compares the result with a threshold nerve impulse value. In an embodiment, the threshold nerve impulse value is pre-configured in the memory module 205 depending on the patient's current heart rate (also known as 'Periodicity'). Further, the data analysis module 202 prepares an analysis report and sends the report to the decision module 203. The analysis report may contain the details on whether the generated total number of nerve impulses exceeds the threshold nerve impulse value or not. In a preferred embodiment, the data analysis module 202 may also be capable of receiving current periodicity of heart rate and compares the current periodicity heart rate with pre-configured normal periodicity value of the heart. Furthermore, the data analysis module 202 sends an analysis report based on the comparison made between two values.

The decision module 203 fetches the analysis report from the data analysis module 202 and takes decision on whether to generate electric charges from the nerve impulses that are produced at the SA node of heart. If the generated total number of nerve impulses exceeds the pre-configured threshold value, the decision module 203 initially allows pre-configured nerve impulses to reach the AV node and then sends the commands to the battery management module 103 to capture the excess nerve impulses. The decision module 203 sends commands to the counting module 201 to count the next nerve impulses that are generated at the SA node if the produced total number of nerve impulses does not exceed the threshold value. Moreover, the decision module 203 is also capable of deciding whether the heart rate is regular and within normal range by using the analyzed report prepared by the data analysis module 202.

The command module 204 sends appropriate commands to the battery management module 103 based on the decisions taken by the decision module 203. In an embodiment, the command module 204 may use any suitable communication channel to send commands to the battery management module 103. The command module 204 may also send necessary commands to the memory module 205 to change the pre-configured threshold values on receiving a request from the user. In a preferred embodiment, the required commands are stored in the memory module 205 of the intelligent monitoring module 102.

Figure 3:
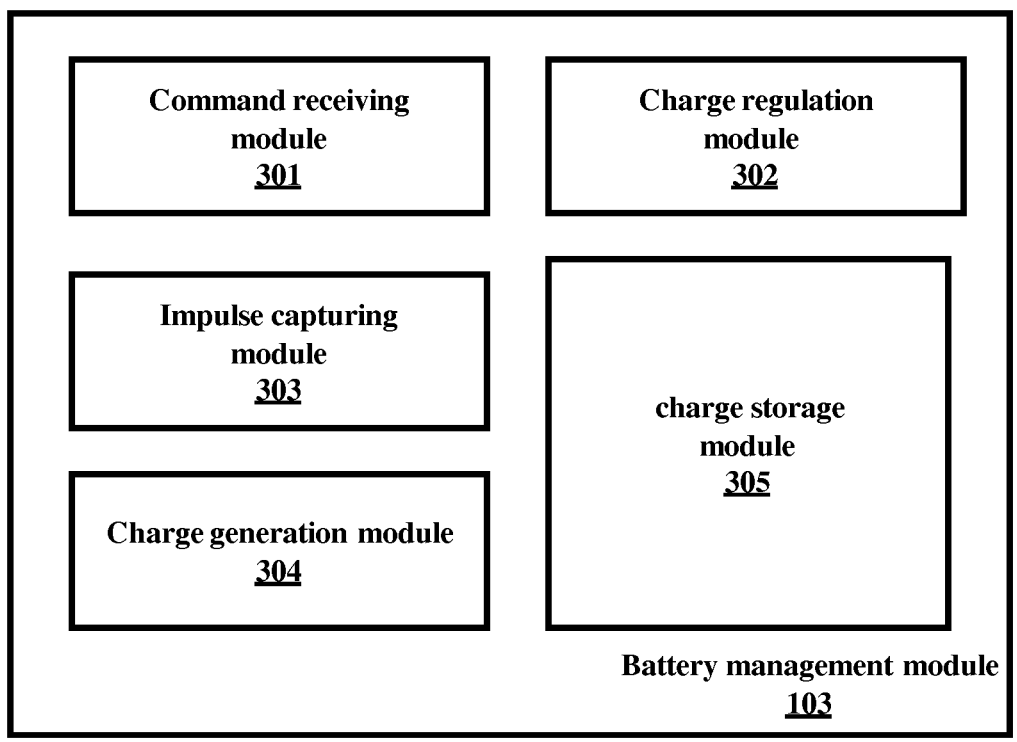
FIG. 3 is a block diagram that shows various components of battery management module, as disclosed in the embodiments herein.

FIG. 3 is a block diagram that shows various components of battery management module, as disclosed in the embodiments herein. The battery management module 103 comprises of a command receiving module 301, a charge regulation module 302, a impulse capturing module 303, a charge generation module 304, and a charge storage module 305.

The command receiving module 301 receives commands from the command module 204 and further sends them to the charge regulation module 302 in order to check the current charge status. On receiving the commands from the command receiving module 301, the charge regulation module 302 logs the charge status and regulates the inflow and outflow of the charges in the charge storage module 305. In an embodiment, the charge storage module 305 stores the generated charge using any suitable device such as but not limited to a battery.

The impulse capturing module 303 receives commands from the command receiving module 301 and accordingly captures specific nerve impulses by using any suitable mechanism. In an embodiment, the impulse capturing module 303 captures specific nerve impulses from the intermodal pathways of the heart by opening a channel between the intermodal pathways and the impulse capturing module 303.

The charge generation module 304 generates electric charges from the captured nerve impulses and stores them in the charge storage module 305. In an embodiment, the charge generation module 304 generates the charges by using any suitable mechanism. The charge storage module 305 can be any charge storage equipment such as but not limited to a battery that allows the IMD 104 to utilize the stored charges whenever it requires.

Figure 4:
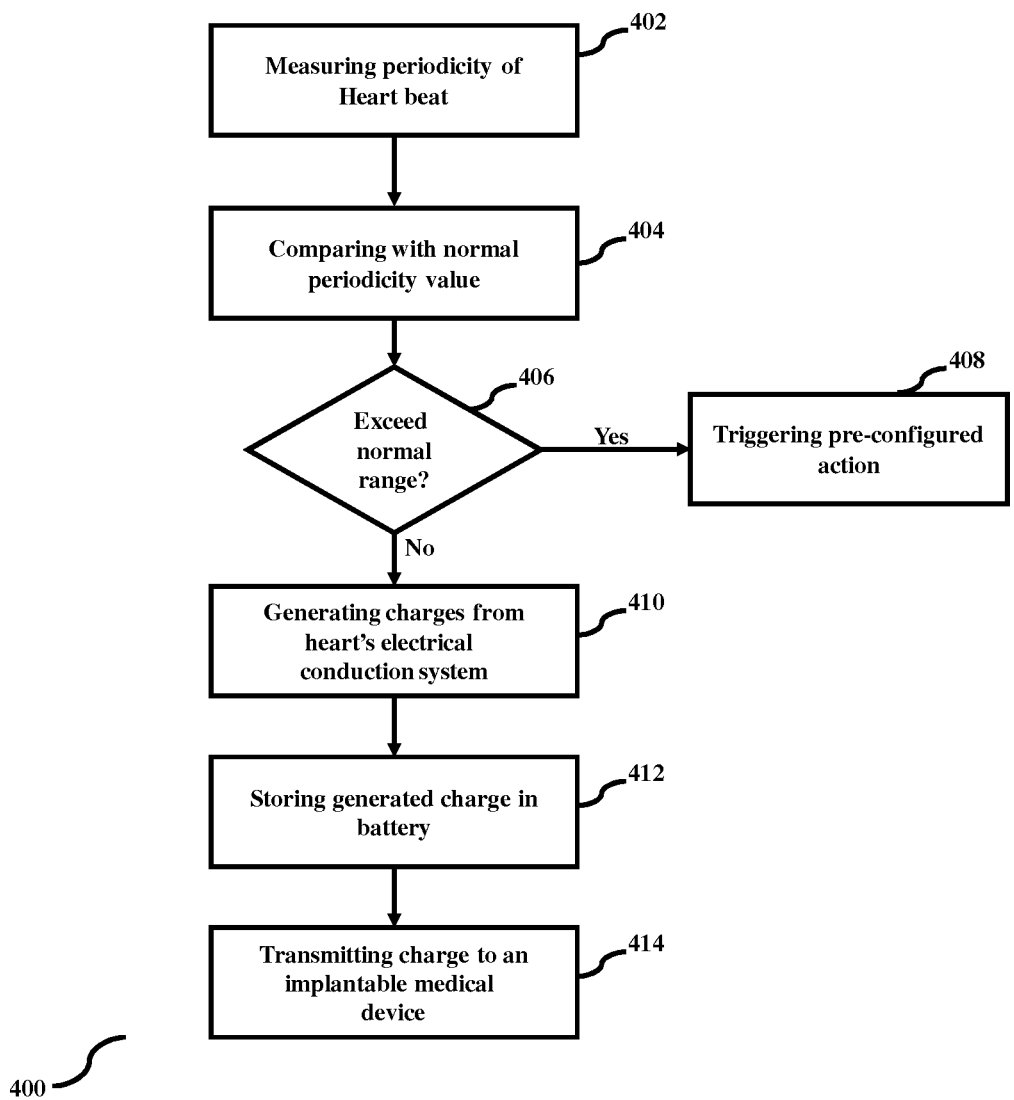
FIG. 4 is a flow diagram which shows various steps involved in the process of generating, storing and transmitting electric charges from heart's electrical conduction system to power an IMD, as disclosed in the embodiments herein.

FIG. 4 is a flow diagram which shows various steps involved in the process of generating, storing and transmitting electric charges from heart's electrical conduction system to power an IMD, as disclosed in the embodiments herein.

Before generating charges from the excess nerve impulses that are produced at the SA node, it is to be confirmed that the heart rate is regular and within the normal range. For confirming the proper functioning of the heart, the normal range of heartbeat (i.e., normal periodicity of heartbeat) has to be pre-configured with the memory module 205. This range may indicate the number of nerve impulses that are required for proper functioning of heart to beat normally. In an embodiment, the normal range of the heartbeat can be pre-configured to the memory module 205 by sending a request to the command module 204. In a preferred embodiment, request to pre-configure this range may be sent to the command module 204 by using any suitable communication channel.

Now, the counting module 201 measures (402) the current periodicity of the heart beat by using any suitable mechanism. In a preferred embodiment, the counting module 201 of the intelligent monitoring module 102 may contain necessary equipments to measure the periodicity of the heart beat automatically before generating electric charges from the excess nerve impulses in the intermodal pathways of the heart. Moreover, the counting module 201 sends the measured periodicity value of the heartbeat to the data analysis module 202 to confirm that the heart rate is regular and within normal range.

In another embodiment, the periodicity of the heart beat can also be measured manually (by using any known techniques available) and the value is given to the data analysis module 202 by sending suitable commands to the command module 204. Later, the command module 204 may send the received periodicity value to the data analysis module 202.

After receiving the current periodicity value of the heartbeat, the data analysis module 202 compares (404) the received periodicity value with the pre-configured normal periodicity value and sends the compared result to the decision module 203. In an embodiment, the data analysis module 202 fetches the normal periodicity value from the memory module 205. Based on the comparison made by the data analysis module 202, the decision module 203 confirms whether the current heart rate is regular or it exceeds the normal range. Further, the decision module 203 decides (406) whether to generate the charges from the excess nerve impulses produced at the SA node or to trigger a pre-configured action.

If the current periodicity value of heart is in normal periodicity range (i.e., heart rate is regular), the decision module 203 sends appropriate commands to the battery management module 103 to capture the excess nerve impulses that are generated at the SA node of the heart. In other case, if the current periodicity value of heart exceeds the normal periodicity value, then the decision module 203 triggers (408) a pre-configured action using the command module 204. The pre-configured action may include alerting the user about the exceeded periodicity of heart rate. The pre-configured action may also include initiating the process of generating the electric charges from excess nerve impulses to power the IMDs 104. This action is very useful to the patients who are having Tachycardia disorder.

Under some particular situations the heart rate in some persons may suddenly increase (over 100 beats per minute) leading to a disorder known as Tachycardia. Due to this, the heart rhythm becomes fast or irregular. As a result, the heart may not able to pump oxygen rich blood in to the body and may increase the risk of stroke, sudden cardiac arrest or may even cause death. This fast rhythm of the heart is due to generation of excess nerve impulses or action potentials at the SA node of the heart. As the generation of electric charges from the excess nerve impulses minimizes the number of nerve impulses that reach the AV node, the increased heart rate may be decreased which further save the life of the patients with Tachycardia.

On receiving the commands from the command module 204, the battery management module 103 captures and generates (410) electric charges from the excess nerve impulses that are produced at the SA node of the heart. While capturing impulses from the intermodal pathways, the charge regulation module 302 logs the current charge status and further regulates the charge flow based on the charge status identified. Later, the charge generation module 304 stores (412) the generated charge in the charge storage module 305. Moreover, the charge storage module 305 can transmit (414) the stored electric charge to the IMD 104 whenever the IMD 104 requires it. In an embodiment, the charge storage module 305 can be connected to the IMD 104 through any suitable communication medium such as but not limited to wireless power transmission using RF technology.

This method of powering the IMDs 104 reduces the number of surgeries that are made to change or recharge the batteries as they get continuous power from the heart's electrical conduction system without affecting heart's normal functionality. In other words, this method acts as a safer alternative to large battery systems that are installed inside the body.

The various actions in method 400 may be performed in the order presented, in a different order or simultaneously. Further, in some embodiments, some actions listed in FIG. 4 may be omitted.

Figure 5:
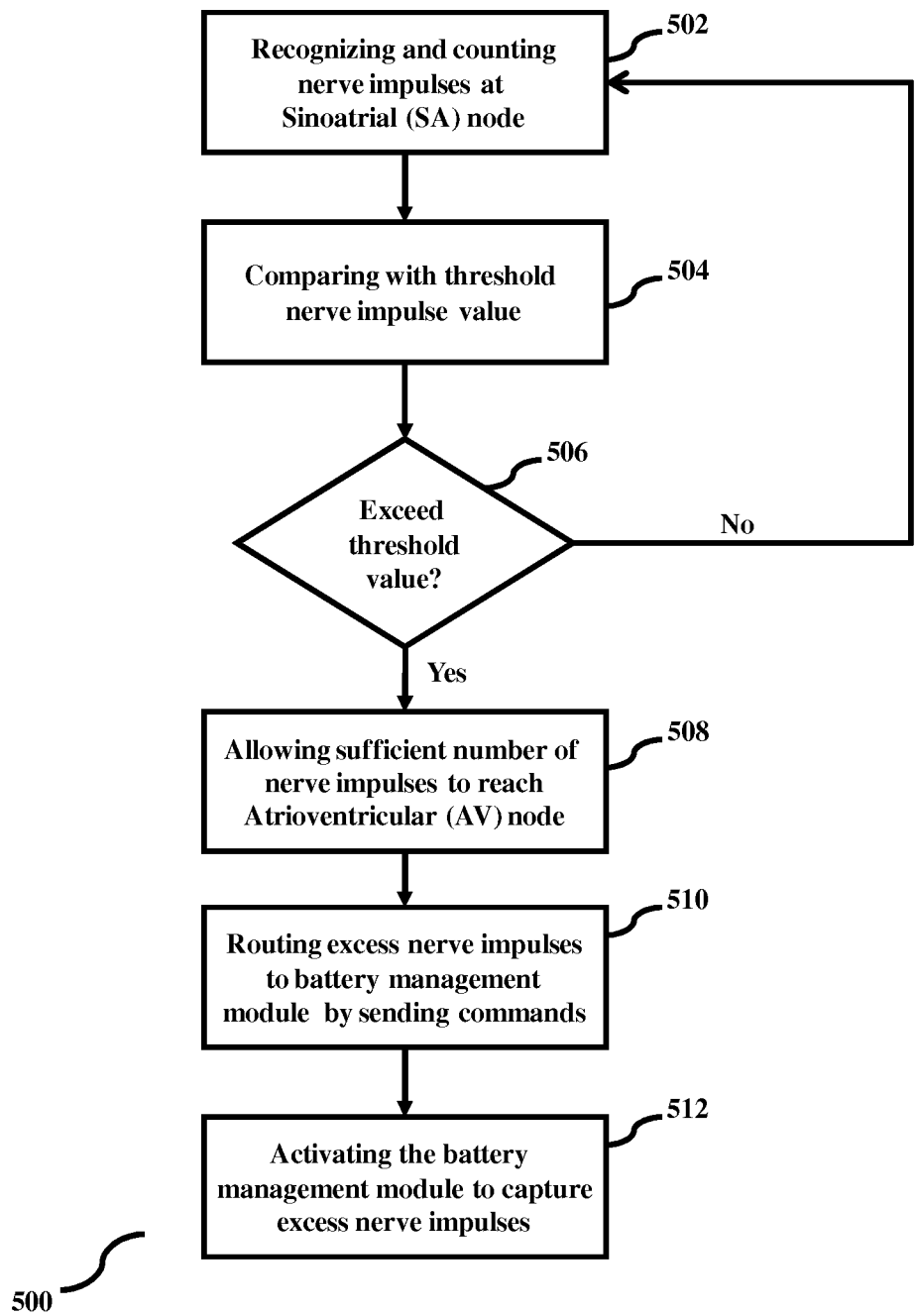
FIG. 5 is a flow diagram which shows various steps involved in the process of generating electric charges from intermodal pathways present in the heart, as disclosed in the embodiments herein.

FIG. 5 is a flow diagram which shows various steps involved in the process of generating electric charges from intermodal pathways present in the heart, as disclosed in the embodiments herein.

Initially, the counting module 201 recognizes (502) the nerve impulses that are read by the voltage detector module 101. Later, the counting module 201 counts (502) the total number of nerve impulses that are produced per heartbeat and sends the result (total count of nerve impulses produced per heart beat) to the data analysis module 202.

After receiving the result from the counting module 201, the data analysis module 202 compares (504) the result with the pre-configured threshold nerve impulse value and checks whether the total count exceeds the threshold nerve impulse value or not. Based on the comparison made, the data analysis module 202 prepares the analysis report and sends it to the decision module 203. Now, the decision module 203 takes decision (506) on whether to generate charges from the available nerve impulses considering the analysis report which is sent by the data analysis module 202. If the total count of the nerve impulses generated exceed the threshold nerve impulse value, the decision module 203 allows (508) sufficient number of nerve impulses to carry message of heart beat to the AV node.

After allowing sufficient number of nerve impulses to the AV node, the decision module 203 routes (510) the excess nerve impulses to the battery management module 103 by sending appropriate commands to the battery management module 103 by using the command module 204. In other case, if the total count of the nerve impulses does not exceed the threshold nerve impulse value, the decision module 203 sends commands to the counting module 201 to count (502) the next nerve impulses that are generated at the SA node.

The command receiving module 301 receives these commands and forwards them to the charge regulation module 302 which regulates the charge flow while capturing the nerve impulses in the charge storage module 305. In a preferred embodiment, the charge regulation module 302 may regulate the captured charges by checking the current charge status in the charge storage module 305.

If the current charge status is maximum i.e. the battery is fully charged, then the charge regulation module 302 stops the impulse capturing module 303 to capture the nerve impulses by sending appropriate commands to the impulse capturing module 303. In other case, if the charge status is not maximum in the charge storage module 305, the charge regulation module 302 allows the impulse capturing module 303 to capture the excess nerve impulses by using the commands that are sent by the command module 204. Moreover, these commands activate (512) the impulse capturing module 303 to capture the excess nerve impulses from the intermodal pathways of the heart. In a preferred embodiment, the excess nerve impulses can be captured by opening the channel that exists between the intermodal pathways and the battery management module 103 which provides flexibility of capturing specific impulses from the heart's electrical conduction system. Later, the charge generation module 304 generates charges from the captured nerve impulses by using any suitable mechanism.

The various actions in method 500 may be performed in the order presented, in a different order or simultaneously. Further, in some embodiments, some actions listed in FIG. 5 may be omitted.

The embodiments disclosed herein can be implemented through at least one software program running on at least one hardware device and performing network management functions to control the network elements. The network elements shown in FIG. 1 to FIG. 3 include blocks which can be at least one of a hardware device, or a combination of hardware device and software module.

The embodiment disclosed herein specifies a system and method for powering IMD's using heart's electrical conduction system. The mechanism allows generating, storing and transmitting electric charges from the heart's electrical conduction system to power the IMD's, providing a system thereof. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in a preferred embodiment through or together with a software program written in e.g. Very high speed integrated circuit Hardware Description Language (VHDL) another programming language, or implemented by one or more VHDL or several software modules being executed on at least one hardware device. The hardware device can be any kind of device which can be programmed including e.g. any kind of computer like a server or a personal computer, or the like, or any combination thereof, e.g. one processor and two FPGAs. The device may also include means which could be e.g. hardware means like e.g. an ASIC, or a combination of hardware and software means, e.g. an ASIC and an FPGA, or at least one microprocessor and at least one memory with software modules located therein. Thus, the means are at least one hardware means and/or at least one software means. The method embodiments described herein could be implemented in pure hardware or partly in hardware and partly in software. The device may also include only software means. Alternatively, the embodiments herein may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims as described herein.

What is claimed is:

1. A method for generating electric charge from electrical conduction system of heart to power up an implantable medical device (IMD), said method comprising:
   measuring periodicity value of heart beat;
   comparing said measured periodicity value with a normal range of periodicity value; and
   generating said electric charge from said electrical conduction system of heart if said measured periodicity value exceeds said normal range of periodicity value.

2. The method as in claim 1, wherein said normal range of periodicity value is pre-configured.

3. The method as in claim 1, wherein said generated electric charge is used to power up said IMD.

4. The method as in claim 1, wherein generating electric charge from said electrical conduction system of heart further comprises of:
   counting number of nerve impulses value at sinoatrial (SA) node of said electrical conduction system of heart;
   comparing said counted number of nerve impulses value with a threshold nerve impulse value;
   identifying at least one excess nerve impulse, wherein said at least one excess nerve impulse refers to additional nerve impulse as compared to said a threshold nerve impulse value; and
   generating said electric charge by converting said at least one excess nerve impulse to electrical charge.

5. The method as in claim 3, wherein said threshold nerve impulse value is pre-configured.

6. A system for generating electric charge for an implanted device from electrical conduction system of heart, said system configured for:
   measuring periodicity value of heart beat using an Implantable Medical Device (IMD) powering system environment;
   comparing said measured periodicity value with a normal range of periodicity value using said IMD powering system environment; and
   generating electric charge from said electrical conduction system of heart if said measured periodicity value exceeds said normal range of periodicity value using said IMD powering system environment.

7. The system as in claim 6, wherein said IMD powering system environment is further configured to provide means for pre-configuring said normal range of periodicity value.

8. The system as in claim 6, wherein said IMD powering system environment is further configured to generate said electric charge from said electrical conduction system of heart by:
   counting number of nerve impulses value at sinoatrial (SA) node of said electrical conduction system of heart using an intelligent monitoring module;
   comparing said counted number of nerve impulses value with a threshold nerve impulse value using said intelligent monitoring module;
   identifying at least one excess nerve impulse using said intelligent monitoring module, wherein said at least one excess nerve impulse refers to additional nerve impulse as compared to said a threshold nerve impulse value;
   routing said at least one excess nerve impulse to a battery management module using said intelligent monitoring module; and
   generating said electric charge by converting said at least one excess nerve impulse to electrical charge using said battery management module.

9. The system as in claim 6, wherein said IMD powering system environment is further configured to provide means for pre-configuring said normal range of periodicity value.

\* \* \* \* \*